US010088414B2

(12) United States Patent
Lipson et al.

(10) Patent No.: US 10,088,414 B2
(45) Date of Patent: Oct. 2, 2018

(54) ON-CHIP INTEGRATED GAS SENSOR BASED ON PHOTONIC SENSING

(71) Applicant: Cornell University, Ithaca, NY (US)

(72) Inventors: Michal Lipson, Ithaca, NY (US); Alexander Gaeta, Ithaca, NY (US); Austin G. Griffith, Ithaca, NY (US); Jaime Cardenas, Ithaca, NY (US); Ryan K. W. Lau, Ithaca, NY (US); Yoshitomo Okawachi, Lansing, NY (US); Romy Fain, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/706,935

(22) Filed: May 7, 2015

(65) Prior Publication Data

US 2015/0323450 A1 Nov. 12, 2015

Related U.S. Application Data

(60) Provisional application No. 61/990,084, filed on May 7, 2014.

(51) Int. Cl.
| | |
|---|---|
| *G01J 5/00* | (2006.01) |
| *G01N 21/3504* | (2014.01) |
| *H01L 31/0232* | (2014.01) |
| *H01L 31/105* | (2006.01) |

(52) U.S. Cl.
CPC ..... *G01N 21/3504* (2013.01); *H01L 31/0232* (2013.01); *H01L 31/02327* (2013.01); *H01L 31/105* (2013.01); *G01N 2201/0612* (2013.01); *G01N 2201/0635* (2013.01)

(58) Field of Classification Search
CPC .................................................. G02F 2203/54
See application file for complete search history.

(56) References Cited

U.S. PATENT DOCUMENTS

| | | | | |
|---|---|---|---|---|
| 2004/0146431 A1* | 7/2004 | Scherer | ............. | G01N 21/7746 422/82.05 |
| 2010/0247029 A1* | 9/2010 | Li | ...................... | G02B 6/12007 385/14 |
| 2010/0329685 A1* | 12/2010 | Zheng | .................. | G02F 1/0147 398/83 |

(Continued)

OTHER PUBLICATIONS

"Mid-infrared optical frequency combs at 2.5 mm based on crystalline micro-resonators" Nat. Commun. 4:1345 doi: 10.1038/ncomms2335 (2013), p. 1-7.*

(Continued)

*Primary Examiner* — Kenneth J Malkowski
(74) *Attorney, Agent, or Firm* — Perkins Coie LLP

(57) ABSTRACT

Techniques, systems, and devices are disclosed to provide on-chip integrated gas sensor based on photonic sensing. For example, a sensing device is provided to include an optical comb generator that produces an optical comb of different optical comb frequencies in a mid-infrared (MIR) spectral range to interact with a sample under detection, the optical comb generator including a substrate, an optical resonator formed on the substrate and an optical waveguide formed on the substrate and coupled to the optical resonator, and an optical detector that detects light from the sample at the different optical comb frequencies.

19 Claims, 9 Drawing Sheets

(56) References Cited

U.S. PATENT DOCUMENTS

2011/0293216 A1* 12/2011 Lipson .............. G02B 6/12007
   385/14

OTHER PUBLICATIONS

Desiatov et al., "Demonstration of submicron square-like silicon waveguide using optimized LOCOS process," Optics Express, vol. 18, No. 18, 2010, pp. 18592-18597.

Gholami et al., "Third-order nonlinearity in silicon beyond 2350 nm," Applied Physics Letters, vol. 99, 2011, pp. 081102-081103.

Pearl et al., "Three photon absorption in silicon for 2300-3300 nm," Applied Physics Letters, vol. 93, 2008, pp. 131102-131103.

Schliesser et al., "Mid-infrared frequency combs," Nature Photonics, vol. 6, 2012, pp. 440-449.

Soref, R., "Mid-infrared photonics in silicon and germanium," Nature Photonics, vol. 4, No. 8, 2010, pp. 495-497.

Sorokin et al., "Sensitive multiplex spectroscopy in the molecular fingerprint 2.4 um region with a Cr(2+):ZnSe femtosecond laser", Optics Express, vol. 15, No. 25, 2007, pp. 16540-16545.

Sun et al., "Composite frequency comb spanning 0.4-2.4μm from a phase-controlled femtosecond Ti:sapphire laser and synchronously pumped optical parametric oscillator," Optics Letters 32(11), 2007, pp. 1414-1416.

Turner-Foster et al., "Ultrashort free-carrier lifetime in low-loss silicon nanowaveguides," Optics Express, vol. 18, No. 4, 2010, pp. 3582-3591.

\* cited by examiner

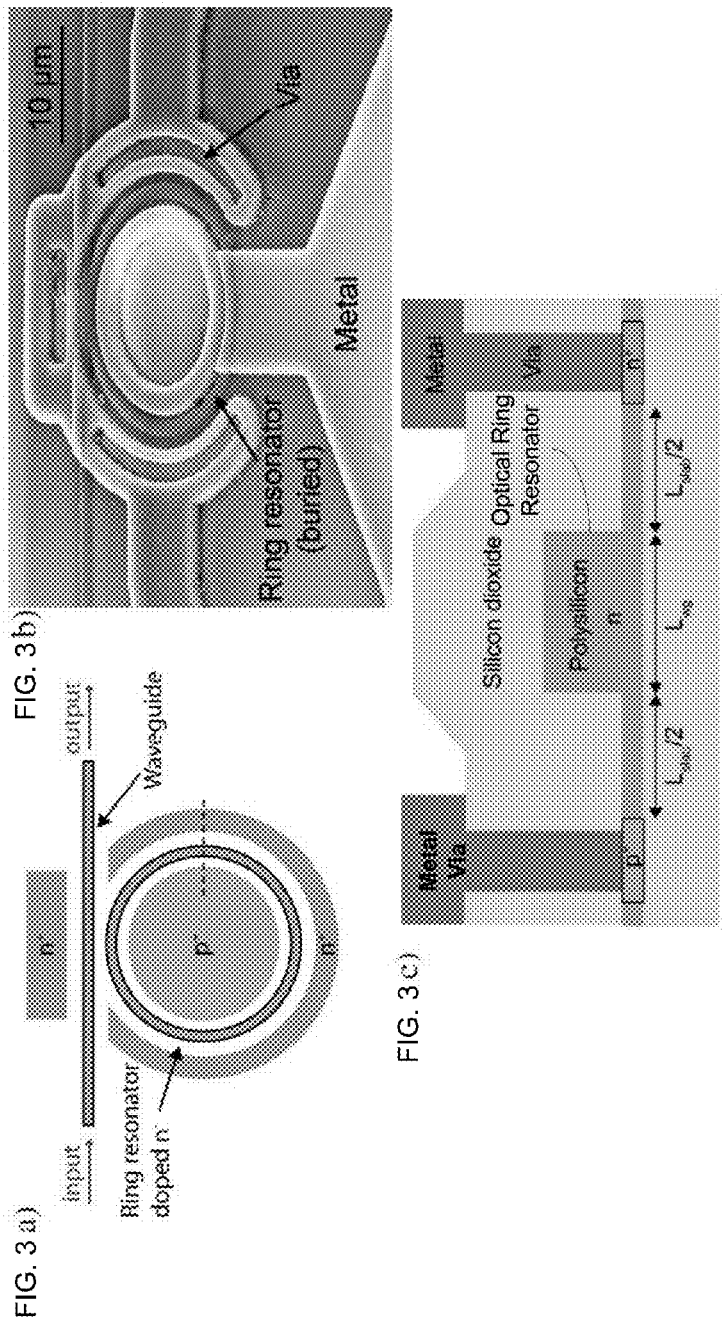

ON-CHIP INTEGRATED GAS SENSOR BASED ON PHOTONIC SENSING

PRIORITY CLAIM AND RELATED PATENT APPLICATIONS

This patent document claims priority and the benefits of U.S. Provisional Application No. 61/990,084 entitled "ON-CHIP INTEGRATED GAS SENSOR BASED ON PHOTONIC SENSING" and filed May 7, 2014, the disclosure of which is incorporated by reference as part of the specification of this document.

STATEMENT REGARDING FEDERALLY SPONSORED RESEARCH OR DEVELOPMENT

This invention was made with government support under Project ID. W31P4Q-13-1-0016 by the Defense Advanced Research Projects Agency (DARPA). The government has certain rights in the invention.

TECHNICAL FIELD

This patent document generally relates to optical devices and techniques for generating optical signals.

BACKGROUND

Nonlinear wave mixing via optical nonlinearities in optical media can be used to generate optical signals. For example, parametric four-wave mixing (FWM) utilizing high-Q microresonators can be used to generate optical frequency combs, which find a wide range of applications including spectroscopy, optical clocks, arbitrary waveform generation, frequency metrology, and astronomical spectrograph calibration. In various implementations of microresonator-based frequency comb generation, a system is optically pumped by an external continuous wave (CW) laser at a specific wavelength corresponding to a cavity resonance of the microresonator in which the FWM occurs. As pump power is coupled into the microresonator, thermal effects can shift the cavity resonance to higher wavelengths, thus creating a soft thermal lock between the cavity resonance and the pump laser. When the intracavity power exceeds the threshold for parametric oscillation, cascaded FWM and higher-order FWM processes occur, resulting in the generation of a frequency comb (i.e., a precisely spaced source of monochromatic frequency components).

SUMMARY

The disclosed technology provides integrated photonic devices for generating optical comb frequencies based on nonlinear optical interaction. In one aspect, the disclosed technology includes integrated photonic chips that can sense gases, particles or other substances. For example, an integrated on chip mid-infrared frequency comb source can be used to detect gases and particles with strong absorption in the MIR spectral range.

In one implementation, a photonic device is provided to include an optical comb generator that produces an optical comb of different optical comb frequencies in a mid-infrared (MIR) spectral range to interact with a sample under detection, the optical comb generator including an integrated circuit that includes a silicon substrate, an optical resonator formed on the silicon substrate via an etchless process by thermal oxidation without etching to achieve a high quality factor in the optical resonator, an PIN junction embedded in the optical resonator, metal contacts formed on the PIN junction and an optical waveguide formed on the substrate and coupled to the optical resonator; and an optical detector that detects light from the sample at the different optical comb frequencies.

In another implementation, a method is provided for fabricating an optical comb generator and includes providing a silicon-on-insulator structure; forming an optical waveguide resonator by performing a thermal oxidation of a silicon part on the silicon-on-insulator structure without etching the silicon to achieve a high quality factor; doping portions of the silicon to provide a PIN junction, the optical waveguide resonator being embedded in the PIN junction; and forming metal contacts for the PIN junction.

The above features and their implementations and variations are described in greater detail in the attached drawings, the description and the claims.

BRIEF DESCRIPTION OF THE DRAWINGS

FIG. 3 includes FIGS. 3a, 3b and 3c, and illustrates an example of an active optical ring based on an electro-optic diode design.

DETAILED DESCRIPTION

Figure 1:
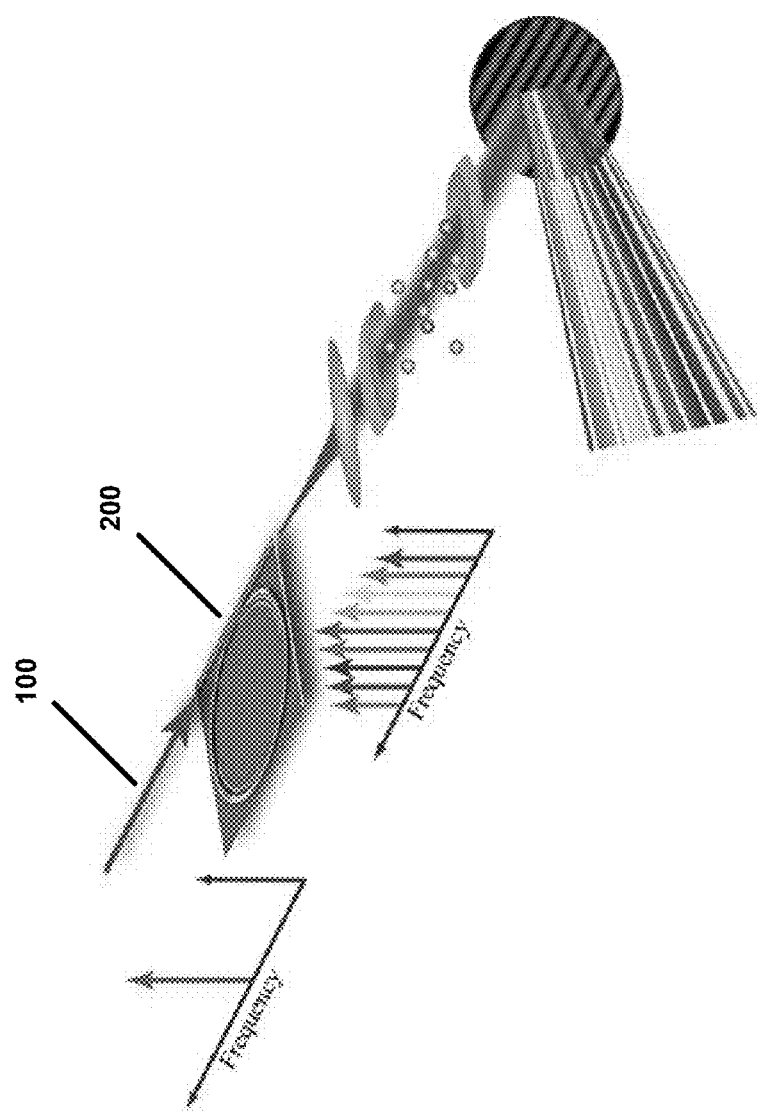
FIG. 1 illustrates an exemplary scheme for detecting gasses using the on-chip MIR comb source.

Various examples of sensing devices are described below to integrate semiconductor integrated chips and detect gases using the mid-infrared frequency (MIR). On-chip MIR combs are more challenging to obtain compared to the recently obtained NIR counterparts since the parametric oscillation threshold is higher in the MIR, due to their larger optical volume of the structure in this wavelength regime. On chip integration means that the proposed device is both robust and compact. On-chip integration and miniaturization of the mid-infrared comb can provide significant advantages in device fabrication, device performance and device operations. For example, such integration may enable high portability for stand-off atmospheric sensing out in the field, and as well as monolithic integration with other necessary components, such as resonant cavities for gas sensing and photo-detectors for measurements. In particular, a complementary CMOS compatible integrated mid-infrared comb source can become less expensive based on the disclosed integration and can simplify the device fabrication and reduce the cost and improve the device reliability for mass production. One of challenges in chip integration associated with on chip mid-infrared comb generation is the difficulty of creating a highly confined and high-quality factor microresonator in semiconductor think film. The disclosed integration technology in this document provides a way for achieving such feature at a reduced cost and with improved performance.

The mid-infrared spectral window is an important spectral range for molecular spectroscopy and chemical/biological sensing. In this wavelength regime the absorption strengths of molecular transitions are 10 to 1000 times greater than those in visible or near infrared, which offers the potential to identify the presence of substances with extremely high sensitivity and selectivity and is thus a powerful tool for scientific, commercial, industrial, and military applications. The increasing concern over environmental effects and the proliferation of sensors networks have heightened interest for devices capable of monitoring in real time a wide range of molecules in real time. Future developments of MIR spectroscopy require the creation of robust coherent sources that can operate with high precision and over a broad bandwidth. Although quantum cascade lasers (QCL) represent an effective source of coherent tunable continuous-wave (cw) lasers in the MIR, they are restricted to only certain types of spectroscopy.

Alternatively, there has been an explosive development of ultra-broadband optical frequency combs (OFC's)—a source of evenly spaced, discrete frequencies of coherent radiation —that can be used for a wide range of applications that require high precision in time and/or frequency and provide a powerful approach to spectroscopy. For example, multi-heterodyne or dual comb spectroscopy can dramatically improve the speed and resolution of acquiring spectroscopic data and enables robust devices without movable parts. Our analysis of many spectroscopy techniques indicates that OFC-based spectroscopy consistently outperforms other methods by orders of magnitude in key figures of merit. Various frequency comb generators tend to operate in the visible or near-infrared and many such devices are based on large femtosecond laser oscillators with frequency spacings that are typically much less than 1 GHz, which is not optimal for various spectroscopic applications.

The disclosed technology can be used to provide an on chip mid-infrared frequency comb source that can be used to detect gases with strong absorption peaks in the MIR.

FIG. 1 illustrates an exemplary scheme for detecting gasses using the on-chip MIR comb source. Optical frequency combs are coherent light sources including discrete lines that are equally spaced in frequency. Mid-infrared comb sources have proved promising for spectroscopy as their broad bandwidth and narrow frequency linewidths make them ideal for probing narrow molecular transitions. Optical frequency combs are a revolutionary light source for high-precision spectroscopy because of their narrow linewidths and precise frequency spacing. Generation of such combs in the mid-infrared spectral region is important for molecular gas detection owing to the presence of a large number of absorption lines in this wavelength regime.

Referring to FIG. 1, a pump laser is provided to supply strong pump 100 into an optical ring structure 200, which is configured to operate as a frequency comb generator that produces the frequencies of the frequency comb. The resulting frequency comb can be used for various applications, including gas detection where the frequency comb is passed through the gas and the absorption is detected.

MIR frequency combs can be implemented by using various pump sources or platforms, e.g., mode locked lasers, free space optical parametric oscillators, and micro-toroid resonators. Supercontinuum generation can be used for generating a broad spectrum in the mid-infrared and can be realized in a number of platforms including silicon waveguides. In various implementations, supercontinuum generation may be implemented by using a high-peak power-pulsed femtosecond source that can generate a broadband coherent spectrum, and for many applications it is desirable to have comb spacings much larger than the ~100 MHz spacing typically produced by such lasers, so that the individual comb lines can be resolved. Quantum cascade lasers may also be used.

On-chip microresonator-based combs present significant advantages because they can generate a broadband frequency comb in a compact and robust integrated platform but the reach of microresonator combs into the mid-infrared has been limited. With a properly phase-matched geometry, a frequency comb can be generated with a high-quality factor microresonator using a single continuous wave (CW) pump laser. Using the parametric $\chi$ nonlinear process of four-wave mixing, energy is transferred from the pump laser into frequency sidebands. Comb lines will be generated at modes supported by the microresonator and lead to an optical frequency comb with a spacing equal to that of the free spectral spacing of the resonant cavity.

In particular, On-chip microresonator-based combs can be engineered with line spacings in the 20-400 GHz range for some applications. Microresonator-based frequency comb sources have been demonstrated in a number of platforms, including silica, quartz, fluoride glasses, silicon nitride, Hydex glass, aluminum nitride and diamond. Mid-infrared microresonator comb generation has been achieved in $MgF_2$ crystalline resonators, generating lines up to 2.55 μm. So far, on-chip mid-infrared comb generation has not been realized because of the difficulty of creating a highly confined and high-quality factor microresonator in semiconductor thin films. Even though silicon, owing to its CMOS compatibility, wide transparency window and high third optical nonlinearity, is an ideal platform for on-chip comb generation deep into the mid-infrared, its linear and nonlinear losses have until now prevented the realization of a silicon microresonator-based comb source.

In etched silicon microresonators, quality factors have been limited by scattering losses because of roughness in the waveguide sidewalls, which is made worse by the high index contrast between waveguide core and cladding. The dominant nonlinear loss in silicon in the 2.2-3.3 μm region is three photon absorption (3 PA), which is a process where three photons are simultaneously absorbed to excite an electron-hole pair. The number of photons lost directly to 3 PA is small (dominated by linear waveguide losses), but the generated free-carrier population will induce significant optical losses.

Some examples of the disclosed technology suggest a particular silicon microresonator to overcome both silicon's high-linear and nonlinear losses. Some examples of the disclosed technology provide fabrication techniques to achieve an on-chip integrated microresonator comb source in the mid-infrared.

Figure 2A:
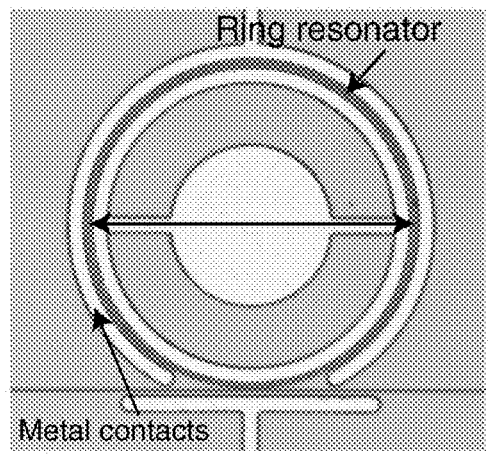
FIGS. 2A and 2B illustrate an example of an optical modulator included in a sensing device.
Figure 2B:
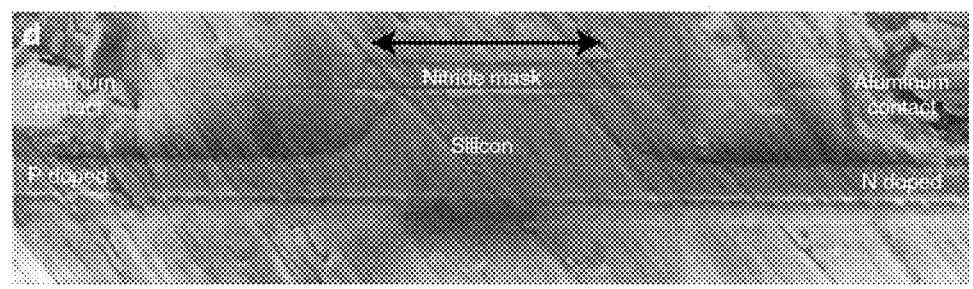

FIG. 2 illustrates an example of an optical modulator included in a sensing device. In some implementations, the optical modulator is a micrometer-scale electro-optic modulator by using a ring resonator embedded in a PIN junction structure. More specifically, FIG. 2A depicts a top plan schematic view of an optical ring structure formed over a substrate including a deposited microelectronic material and FIG. 2B shows a scanning electron microscope (SEM) image of the device in FIG. 2A where the structures and locations of a silicon waveguide, doped regions and metal contacts of a slice of the ring resonator in FIG. 2A are shown. Various material can be used to construct the resonator medium besides silicon (germanium, silicon nitride, etc.), as long as the material losses are low in the MIDIR and the nonlinearity is strong enough to achieve oscillation. The resonator can be in other resonator configurations different from a ring resonator and various on chip resonator cavity designs can be used. We pump our ring with an off chip laser source, and detect comb lines off chip in a FTIR. This can be accomplished on chip using a bonded laser and integrated photodetectors.

The substrate may be formed to include silicon, germanium, or a compound semiconductor such as gallium arsenide or indium phosphide. An optical waveguide is formed on the substrate close to the ring resonator to be optically coupled with the ring resonator by optical evanescent coupling to provide input light to the ring resonator and output light out of the ring resonator. An electrical signal is applied to the PIN diode structure to control the carrier injection and optical modulation using the free carrier dispersion effect. This electrical signal can be used to change or control the resonant wavelength of the optical ring resonator, thus changing or controlling the optical transmission of an optical signal output by the optical waveguide.

FIG. 3 illustrates an example of an active optical ring based on an electro-optic diode design that can be used to implement the device structure in FIGS. 2A and 2B. This active ring can be configured as a micrometer-scale electro-optic modulator by using a polysilicon ring resonator of a radius of 20 µm or 10 µm embedded in a 40 nm-tall $p^+n^-n^+$ diode structure and laterally coupled to a polysilicon waveguide. In a prototype sample device, the modulator can be operated at 2.5 Gbps and 10 dB extinction ratio. In addition, this device can be fabricated using the Excimer Laser Annealing (ELA) process to be operated at 3 Gbps. The polycrystalline silicon material exhibits properties that simultaneously enable high quality factor optical resonators and sub-nanosecond electrical carrier injection. An embedded $p^+n^-n^+$ diode can be used to achieve optical modulation using the free carrier plasma dispersion effect. Active optical devices in a deposited microelectronic material can break the dependence on the traditional single layer silicon-on-insulator platform and help lead to monolithic large-scale integration of photonic networks on a microprocessor chip.

FIG. 3 includes FIG. 3a, FIG. 3b and FIG. 3c. More specifically, FIG. 3a depicts a top plan schematic view of an electro-optic modulator formed over a substrate formed of a deposited microelectronic material, such as polycrystalline silicon (i.e. polysilicon), for example. In other implementations, the substrate may be formed from at least one of another form of silicon, germanium, or a compound semiconductor such as gallium arsenide or indium phosphide, for example. Electro-optic modulator includes an optical ring resonator doped with $n^-$, a p-type doped semiconducting region ($p^+$) inside the ring resonator, and another n-type doped semiconducting region ($n^+$) outside the ring resonator so that the $n^-$-doped ring resonator is sandwiched between the inner semiconducting region ($p^+$) and the outer semiconducting region ($n^+$) to form the embedded $p^+n^-n^+$ diode structure. An optical waveguide is formed on the substrate close to the ring resonator to be optically coupled with the ring resonator by optical evanescent coupling to provide input light to the ring resonator and output light out of the ring resonator. An additional n-type doped semiconducting region ($n^+$) is formed on the other side of the optical waveguide to so that the segment of the ring resonator closest to the optical waveguide is also in the $p^+n^-n^+$ diode structure. An electrical signal is applied to the $p^+n^-n^+$ diode structure to control the carrier injection and optical modulation using the free carrier dispersion effect. This electrical signal can be used to change or control the resonant wavelength of the optical ring resonator, thus changing or controlling the optical transmission of an optical signal output by the optical waveguide.

FIG. 3b shows a scanning electron microscope (SEM) image of the device in FIG. 4a where a ring polysilicon resonator and 450 nm-wide bus waveguide are buried under 1 µtm silicon dioxide. FIG. 3c further show a cross-section schematic of the device (not to scale) in FIG. 4a.

Figure 4:
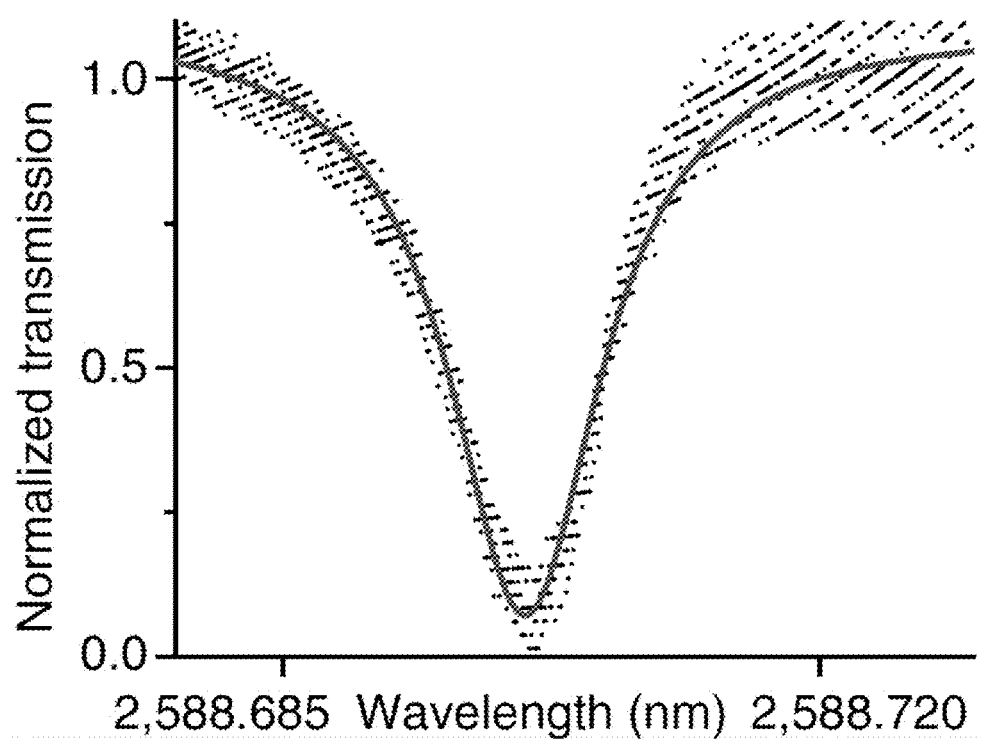
FIG. 4 shows an experimental transmission spectrum measured from the optical modulator of FIGS. 2A and 2B.

FIG. 4 shows an experimental transmission spectrum measured from the optical modulator of FIGS. 2A and 2B. As shown in FIG. 4, an ultra-high Q ring resonator in the MIR is provided based on high confinement waveguides with propagation losses of less than 0.8 dB/cm. The waveguide dimensions (500 nm by 1400 nm) are designed to achieve anomalous and low dispersion from 2200 nm to 3000 nm, which is critical in order to demonstrate four wave mixing gain over this spectral range. The measured experimental transmission spectrum has an intrinsic Q=510,000 measured using low input power (<100 uW), which to our knowledge is the highest demonstrated quality factor in the MIR for a silicon microresonator.

Figure 5:
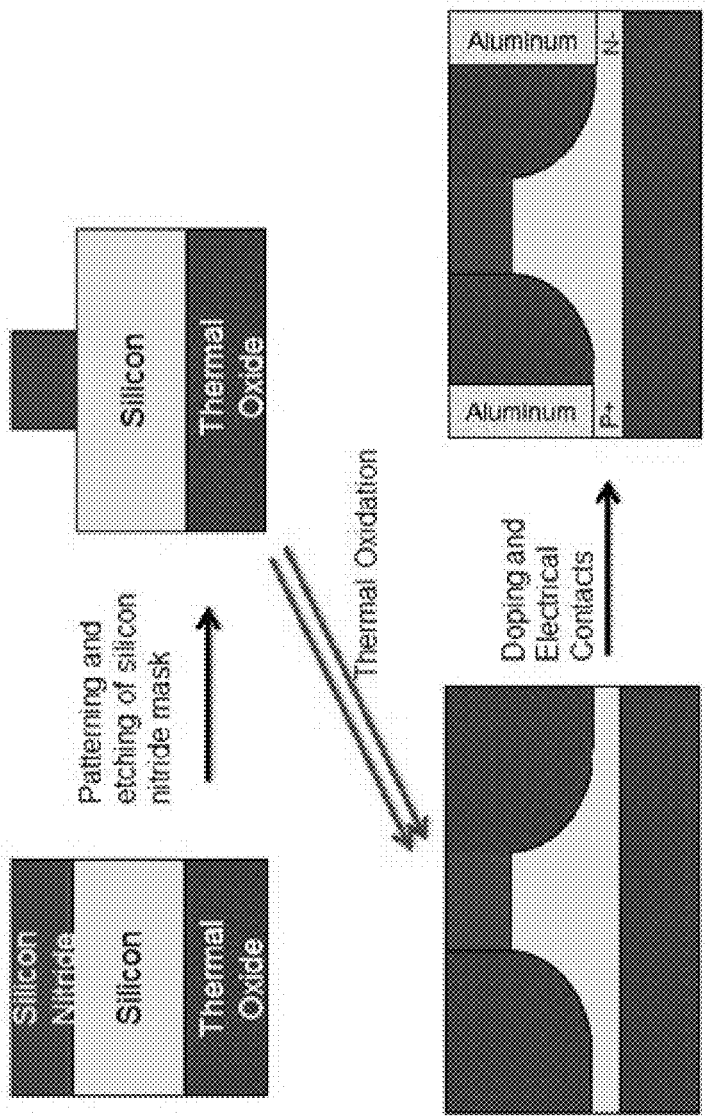
FIG. 5 shows an example of a fabrication process for a silicon waveguide included in a sensing device.

FIG. 5 shows an example of a fabrication process for a silicon waveguide embedded in PIN junction.

In some implementations, an etchless process is proposed to overcome the linear losses of etched silicon waveguides. The etchless process achieves ultra-low loss waveguiding structures. The etchless process employs thermal oxidation instead of etching to fabricate the silicon waveguide. The process stars by preparing a commercial silicon-on-insulator structure. In some implementations, the silicon-on-insulator structure may have a top layer of 500 nm of silicon and a buried oxide of 3 um. In some implementations, silicon as a nonlinear medium may demonstrate a n2 of $10^{-14}$ cm$^2$/W at 2.5 µm that is two orders of magnitude higher than SiO2 and is transparent from 1200 nm to past 6 um.

Next, a low-pressure chemical vapor deposition may be performed to deposit silicon nitride over the silicon-on-insulator structure. In some implementations, silicon nitride has 200 nm thickness. The silicon nitride mask may be then patterned using, for example, electron beam lithography and resist, and etched using reactive ion etching. Thermal oxidation may be performed to form the etchless silicon waveguide. The waveguide is then clad with plasma enhanced chemical vapor deposition silicon dioxide, and the vias are etched into the oxide. The silicon slab is doped with phosphorous and boron to form a p-region and an n-region which form a PIN diode. This PIN structure operates to efficiently extract free carriers. Metal contacts are formed by, for example, sputtering Aluminum. In order to achieve dispersion engineering for comb generation, in some implementations, the silicon nitride is patterned at, for example, 1.4 um wide.

Since the etching process introduces roughness and absorption sites into waveguide sidewalls, the proposed etchless process results in low optical losses in a high confinement waveguide required for high nonlinearity and dispersion engineering. In order to overcome the nonlinear losses of silicon (mainly three photon absorption followed by free carrier generation), the waveguides are embed in the ring structure in a PIN structure to reduce free carrier lifetimes. In some implementations, at the power levels for comb generation (typically 2-3 W in our cavity), free carrier losses would be above 1 dB/cm without the PIN and less than 0.1 dB/cm with the reverse PIN. The etchless process is particularly useful here, due to the need for a silicon slab for electrical integration. As the slab surface is never etched, it is possible to avoid the high losses typically associated with active silicon resonators.

Figure 6A:
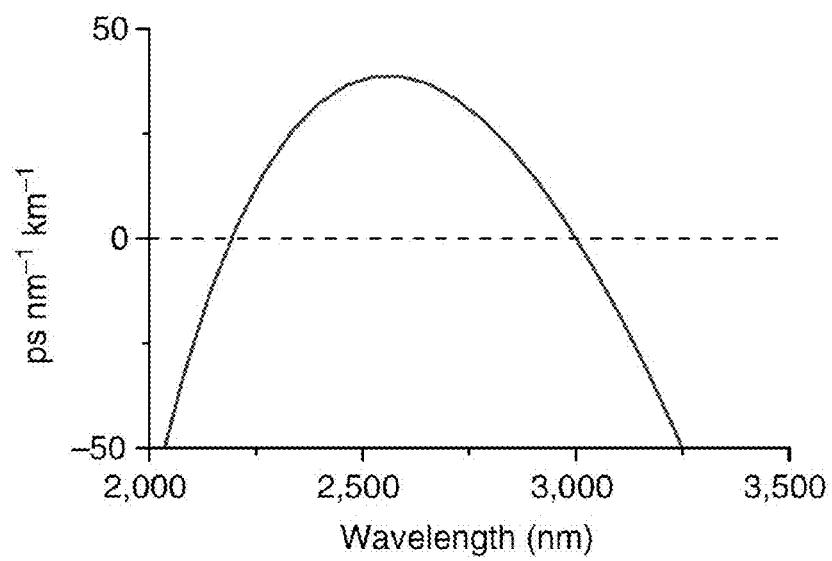
FIGS. 6A and 6B show dispersion engineering and simulated comb bandwidth for a silicon microresonator.
Figure 6B:
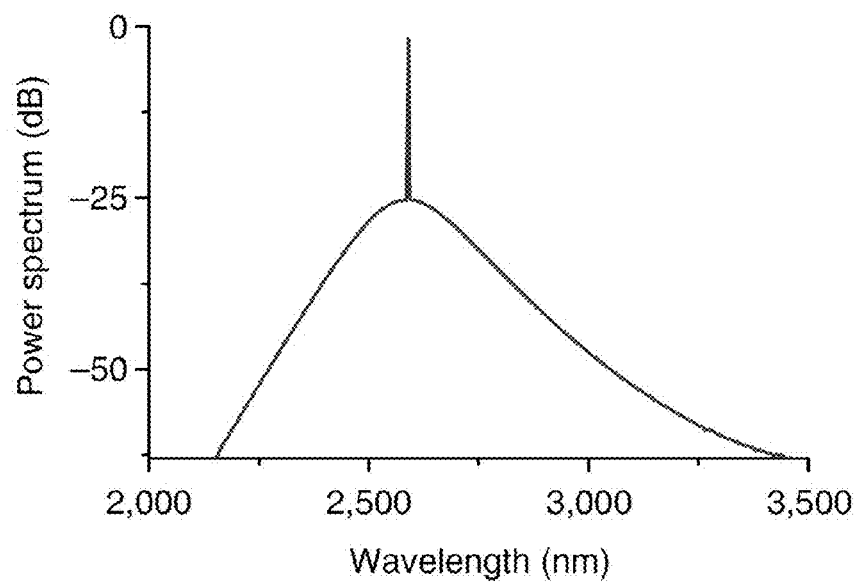

To enable broadband comb generation, in some implementations, the etchless waveguide geometry is configured to have anomalous group velocity dispersion from 2.2 to 3 μm. The geometry of the silicon waveguide governs the bandwidth of the frequency comb as the waveguide cross-section determines its dispersion profile. The simulated group velocity dispersion is shown in FIG. 6A. The commercial software Silvaco Athena is used to simulate the oxidation process, to obtain the waveguide profile. From repeated tests, we have found good agreement between the simulated waveguide profile and the actual etchless waveguide formed. The simulated bandwidth for a frequency comb generated in this geometry is shown in FIG. 6B, for 150 mW of optical power in the bus waveguide and an assumed 10 ps free-carrier lifetime.

To simulate the spectral-temporal dynamics of the microresonator combs, a recently developed numerical approach is used based on the Lugiato-Lefever equation. Here, the method to take into account multi-photon absorption and the free-carrier dynamics on the generated optical spectra is slightly modified. This adds additional loss terms (free-carrier and 3 PA) to the Lugiato-Lefever equation, as well as a term for the dispersive effects of the free-carriers. With the free-carrier population kept at low levels (10 ps lifetime), simulations predict that generation of a coherent frequency comb in this geometry is possible.

To mitigate silicon's nonlinear loss, we embed the silicon microresonator in a reverse biased positive-intrinsic-negative (PIN) doped junction to sweep out carriers generated from three-photon absorption. Significant free-carriers accumulate when pumping a passive silicon waveguide with a CW laser, limited only by the natural free-carrier lifetime of the structure. Here, we counteract the carrier generation while using a CW pump by extracting the generated carriers using a PIN junction operated in reverse bias. The PIN junction prevents the electrical injection of carriers into the waveguide while allowing generated free carriers to be swept out—with effective free-carrier lifetimes demonstrated as short as 12 ps.

Figure 7:
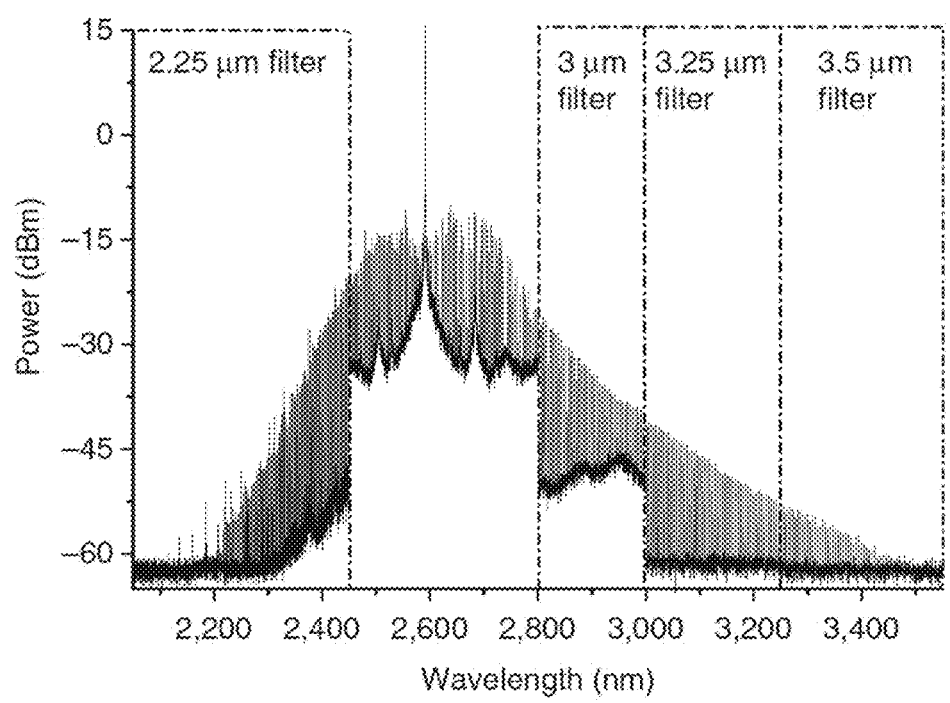
FIG. 7 shows MIR optical frequency comb generation from an etches silicon microresonator

FIG. 7 shows MIR optical frequency comb generation from an etches silicon microresonator. Broadband frequency comb generation from 2.1 to 3.5 μm in the etchless silicon micro-resonator is obtained. This frequency comb is generated with 150 mW of optical power in the bus waveguide, and with a 10V reverse bias applied on the PIN junction. The frequency spacing of the comb is 127 Ghz. Owing to the limited dynamic range of the optical spectrum analyser, the frequency comb was measured using a series of optical filters.

Figure 8A:
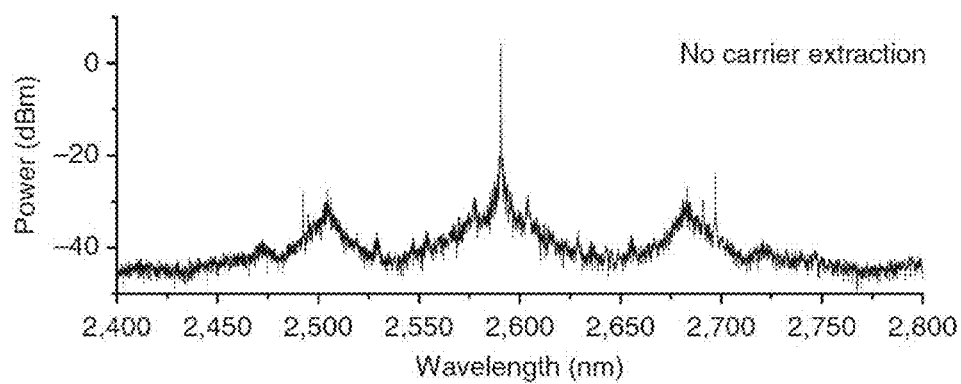
FIGS. 8A and 8B illustrate comparison charts showing the effect of carrier extraction on frequency comb generation.
Figure 8B:
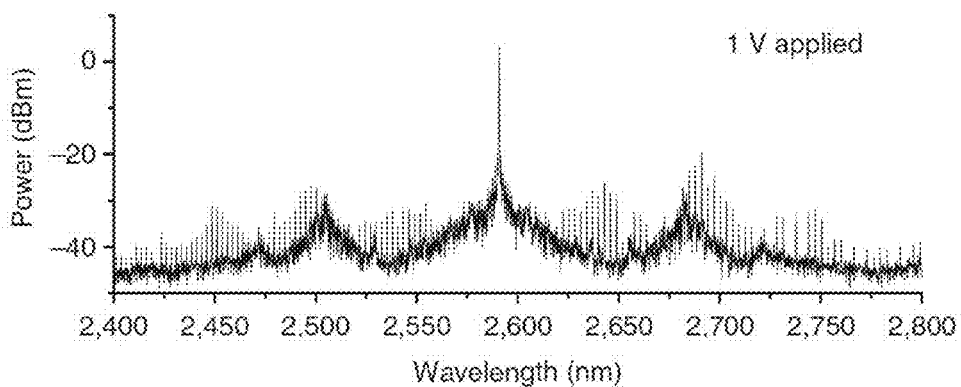

FIG. 8 includes FIGS. 8A and 8B, and illustrates comparison charts showing the effect of carrier extraction on frequency comb generation.

The effect of three photon absorption on frequency comb generation depends strongly on the bias voltage of the PIN structure. The broad peaks at 2,510 and 2,685 nm are artefacts of the FTIR. FIG. 8A shows that with the pump set at a fixed wavelength and the voltage source off, only a few lines are generated near 2,500 and 2,700 nm at this detuning. FIG. 8B shows, hundreds of comb lines are generated across the spectrum by applying even a small voltage in reverse bias to the junction.

In some implementations, to generate comb lines for spectroscopy, 2.6 um light is coupled into the resonator via a waveguide. The light can either come from an on chip source (bonded laser), or off chip using a fiber. Reverse bias voltage is applied to the PIN diode to extract generated free carriers to allow oscillation.

Figure 9:
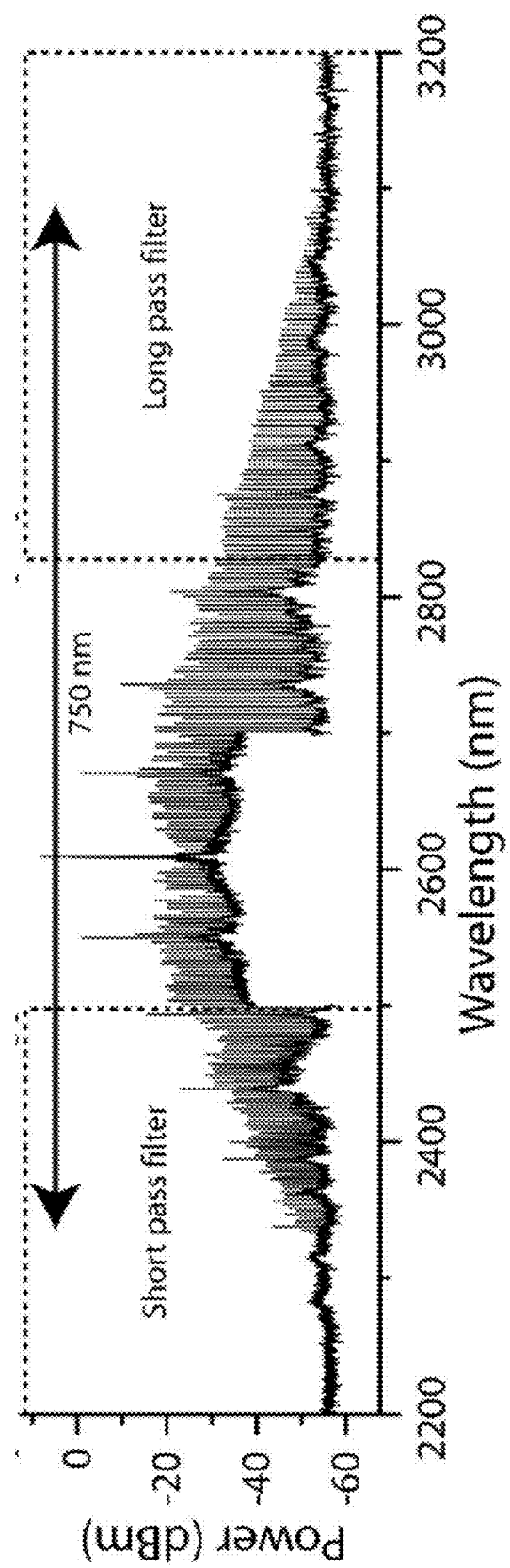
FIG. 9 illustrates FTIR scans showing the full extent of the MIDIR frequency comb.

FIG. 9 illustrates FTIR scans showing the full extent of the MIDIR frequency comb.

The comb is measured using a FTIR which has a limited dynamic range, and therefore requires the use of short and long pass filters in order to filter the pump and measure the full comb. A broadband frequency comb spanning from 2350 to 3100 nm is generated using the etchless platform. In some implementations, 10 volts are applied to the PIN junction in reverse bias to extract carriers generated from three-photon absorption. In order to generate the comb, the input pump wavelength is adjusted until the input pump wavelength is on resonance with the optical ring structure. By gradually increasing the input power into the waveguide, an oscillation threshold is measured for the silicon resonator. In one example, 3.1+/−0.6 mW is measured. At full comb generation, 1 mA of current is tracted from the PIN junction, which demonstrates the need for the reverse PIN structure in this platform. Without carrier extraction (i.e., under no applied voltage), only 8 comb lines are generated.

Gas sensing can be accomplished by passing the generated comb through the gas, either via an air-clad waveguide, leaving the resonator unclad, or just passing the light in free space through an opening in the chip. Detecting the power left in the comb can be achieved by measuring the power of each comb line, either by wavelength division multiplexing to either on chip or off chip photo-detectors, or an off chip optical spectrum analyzer.

In addition, a proposed sensing device can be thermally tuned to sweep the comb lines in frequency, allowing for high resolution spectroscopy to be achieved in a low resolution device. Since comb lines generated by a parametric process are incredibly narrow, very precise absorption features can be detected by such a scheme.

The comb can also be phase locked to a known reference to achieve absolute wavelength referencing of absorption—which is necessary if there are two gases that are close together in absorption spectra. In addition, this could be used to determine between two close isotopes of the gas.

The described gas sensing devices can be used to detect gases with strong absorption in the MIR. Uses include: contaminate detection in commercial fabrication or manufacturing, poison gas sensing for civilian or military usage in the field, air quality monitors, biological specimen testing, testing for microbes with MIR absorbing dyes.

Optical frequency comb generation can be achieved in various ways. For example, a continuous wave pump laser external to a microresonator can be used to optically pump the microresonator to cause nonlinear four-wave mixing (FWM) for the optical comb generation. In this method, however, fluctuations in the frequency or power of the continuous-wave (CW) pump laser can disrupt the thermal lock for the optical comb generation. This disruption of thermal lock disrupts the comb generation.

The above disclosed technology provides a unique integrated platform by fusing two previously seemingly incompatible features in an integrated package in silicon and under the CMOS fabrication processing: the feature of making an electrically integrated ring resonator with a high quality factor and the silicon etching process that tends to degrade the silicon boundary surface quality, thus leading to a lower resonator quality factor. In this regard, the active integration of a silicon resonator requires a silicon slab and electrically active silicon optical devices to date have slabs that are fabricated by etching—leaving the surface of the silicon slab highly damaged from the etching process. In the disclosed technology, the efficient comb generation uses an etchless process to fabricate devices with a suitable waveguide geometry for electrical integration and comb generation. The disclosed technology was used to demonstrate the first electrically integrated etchless device, and shows that electrical integration can be achieved without compromising the high quality factor of the etchless process.

Therefore, a photonic device is provided to include an optical comb generator that produces an optical comb of different optical comb frequencies in a mid-infrared (MIR) spectral range to interact with a sample under detection, the optical comb generator including a substrate, an optical resonator formed on the substrate and an optical waveguide formed on the substrate and coupled to the optical resonator; and an optical detector that detects light from the sample at the different optical comb frequencies. The fabrication begins with a silicon-on-insulator wafer with a top layer of silicon and a buried oxide. A low-pressure chemical vapor deposition is used to deposit silicon nitride on the wafer. The silicon nitride mask is then patterned using electron beam lithography and resist, and etched using reactive ion etching, followed by thermal oxidation to form the etchless silicon waveguide. The waveguide is then clad with plasma enhanced chemical vapor deposition silicon dioxide, and the vias are etched into the oxide. Next, the PIN junction is formed. This process enables simultaneously achieving high quality factor in the waveguide while providing electrical integration.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Only a few implementations and examples are described and other implementations, enhancements and variations can be made based on what is described and illustrated in this patent document.

What is claimed is what is described and illustrated, including:

1. A photonic device, comprising:
   an optical comb generator that produces an optical comb of different optical comb frequencies in a mid-infrared (MIR) spectral range to interact with a sample under detection, wherein the optical comb generator is a CMOS compatible device including an integrated circuit that includes a silicon substrate, an optical resonator formed on the silicon substrate, a PIN junction embedded in the optical resonator, metal contacts formed on the PIN junction and an optical waveguide formed on the substrate and coupled to the optical resonator, wherein the optical comb generator is operable to reduce free carrier loss to 0.1 dB/cm or less; and
   an optical detector that detects light from the sample at the different optical comb frequencies,
   wherein the PIN junction includes a first doped region located inside the optical resonator and having a first conductivity, a second doped region located inside the optical resonator and having a second conductivity, and a third doped region located outside the optical resonator and having the first conductivity.

2. The device as in claim 1, wherein the optical detector is formed on the substrate.

3. The device as in claim 1, wherein the optical detector is formed outside the substrate.

4. The device as in claim 1, wherein the optical waveguide includes a silicon material.

5. The device as in claim 1, wherein the PIN junction includes a p-doped region on one side of the optical resonator and an n-doped region on an opposing side of the optical resonator.

6. The device as in claim 1, wherein the optical resonator has a ring shape.

7. The device as in claim 1, wherein the substrate includes a silicon-on-insulator structure and the optical resonator is formed of a silicon part and is embedded in the PIN junction.

8. The device as in claim 1, wherein light is coupled into the optical resonator via the waveguide, the light coming from an on chip source or off chip source.

9. The device as in claim 1, wherein the optical detector is provided for contaminate detection, air quality monitors, biological specimen testing, or testing for microbes with MIR absorbing dyes.

10. The device as in claim 1, further comprising an additional doping region formed on an opposing side of the optical waveguide to the ring resonator.

11. The device as in claim 10, the additional doping region has the first conductivity.

12. The device as in claim 10, the first doped region has less concentration of impurities than that of the third doped region.

13. The device as in claim 1, wherein the optical resonator is formed on the silicon substrate via an etchless process by thermal oxidation without etching to achieve a high quality factor in the optical resonator.

14. A method of fabricating an optical comb generator, comprising:
   providing a silicon-on-insulator structure;
   forming an optical waveguide resonator by performing a thermal oxidation of a silicon part on the silicon-on-insulator structure without etching the silicon to achieve a high quality factor;
   doping portions of the silicon to provide a PIN junction, the optical waveguide resonator being embedded in the PIN junction; and
   forming metal contacts for the PIN junction,
   wherein the doping of the portions of the silicon includes providing a first doped region located in the optical waveguide resonator and having a first conductivity, providing a second doped region located inside the optical waveguide resonator and having a second conductivity, and providing a third doped region located outside the optical waveguide resonator and having the first conductivity, and wherein the first doped region has less concentration of impurities than that of the third doped region.

15. The method of claim 14, the providing of the optical waveguide includes:
   depositing silicon nitride over the silicon-on-insulator structure; and
   patterning the silicon nitride to form a silicon nitride mask.

16. The method of claim 14, further comprising:
   forming the metal contacts by using metal vias.

17. A method of operating a photonic device, comprising:
   providing an optical comb generator including an integrated circuit that includes a silicon substrate, an optical resonator formed on the silicon substrate, a PIN junction embedded in the optical resonator, metal contacts formed on the PIN junction and an optical waveguide formed on the substrate and coupled to the optical resonator, wherein the optical resonator is located on a first side of the optical waveguide and an additional doping region is formed on a second side of the optical waveguide, the second side opposing to the first side, wherein the optical comb generator is a CMOS compatible device; and
   operating an optical comb generator to produce an optical comb of different optical comb frequencies in a mid-infrared (MIR) spectral range to interact with a sample under detection, wherein the operating of the optical comb generator includes:
      providing a reverse bias to the PIN junction to extract carriers generated therein; and
      directing pump light at a pump frequency into the optical resonator to cause nonlinear optical interactions to generate optical comb frequencies,
   wherein the operating the optical comb generator includes reducing free carrier loss to 0.1 dB/cm or less.

18. The method of claim 17, wherein the optical comb frequencies are in a mid-infrared (MIR) spectral range to interact with a sample under detection.

19. The method of claim 17, further comprising:
   directing the optical comb frequencies into a gas sample to obtain optical measurements of the gas sample.

* * * * *